(12) United States Patent
Harimoto et al.

(10) Patent No.: US 12,202,969 B2
(45) Date of Patent: Jan. 21, 2025

(54) POLYMER COMPOSITION, MOLDED BODY, AND NERVE REGENERATION INDUCING TUBE

(71) Applicant: Toray Industries, Inc., Tokyo (JP)

(72) Inventors: Kenichi Harimoto, Otsu (JP); Kanta Tanabe, Otsu (JP); Kazuhiro Tanahashi, Otsu (JP); Hirokazu Sakaguchi, Otsu (JP)

(73) Assignee: Toray Industries, Inc., Tokyo (JP)

( * ) Notice: Subject to any disclaimer, the term of this patent is extended or adjusted under 35 U.S.C. 154(b) by 681 days.

(21) Appl. No.: 17/612,068

(22) PCT Filed: May 26, 2020

(86) PCT No.: PCT/JP2020/020695
§ 371 (c)(1),
(2) Date: Nov. 17, 2021

(87) PCT Pub. No.: WO2020/241624
PCT Pub. Date: Dec. 3, 2020

(65) Prior Publication Data
US 2022/0251372 A1    Aug. 11, 2022

(30) Foreign Application Priority Data
May 30, 2019    (JP) ................. 2019-100951

(51) Int. Cl.
*C08L 67/04*    (2006.01)
*A61L 27/26*    (2006.01)
(Continued)

(52) U.S. Cl.
CPC .............. *C08L 67/04* (2013.01); *A61L 27/26* (2013.01); *A61L 27/58* (2013.01); *C08G 63/08* (2013.01);
(Continued)

(58) Field of Classification Search
CPC ...... C08L 67/04; C08L 2205/02; A61L 27/26; C08G 63/08
See application file for complete search history.

(56) References Cited

U.S. PATENT DOCUMENTS

| 6,573,340 B1 | 6/2003 | Khemani et al. |
| 11,078,327 B2 | 8/2021 | Kakizawa et al. |
| 2004/0039441 A1 | 2/2004 | Rowland et al. |

FOREIGN PATENT DOCUMENTS

| EP | 3461857 A1 * | 4/2019 | ............ A61L 27/18 |
| JP | 2005-525911 A | 9/2005 | |

(Continued)

OTHER PUBLICATIONS

D.W. Grijpma et al., "Polymerization temperature effects on the properties of l-lactide and ε-caprolactone copolymers," Polymer Bulletin, vol. 25, pp. 335-341 (1991) Abstract.

*Primary Examiner* — Marc S Zimmer
*Assistant Examiner* — Surbhi M Du
(74) *Attorney, Agent, or Firm* — DLA Piper LLP (US)

(57) ABSTRACT

A polymer composition contains polylactic acid and a dilactide/ε-caprolactone copolymer, in which a content of the polylactic acid relative to a total of 100 mass % of the polylactic acid and the dilactide/ε-caprolactone copolymer is 20 to 40 mass %, and in which the dilactide/ε-caprolactone copolymer satisfies (1) an R value represented by a following formula is 0.45 or more and 0.99 or less:

$$R = [AB]/(2[A][B]) \times 100$$

where [A] is a molar fraction (%) of a dilactide residue in the dilactide/ε-caprolactone copolymer, [B] is a molar fraction (%) of an ε-caprolactone residue in the dilactide/ε-capro- (Continued)

lactone copolymer, and [AB] is a molar fraction (%) of a structure in which a dilactide residue and an ε-caprolactone residue are adjacent to each other (A-B and B-A) in the dilactide/ε-caprolactone copolymer, and (2) at least one of the dilactide residue and the ε-caprolactone residue has a degree of crystallization of less than 14%.

14 Claims, 5 Drawing Sheets

(51) Int. Cl.
    *A61L 27/58*     (2006.01)
    *C08G 63/08*     (2006.01)
    *C08G 63/78*     (2006.01)

(52) U.S. Cl.
    CPC ........ *C08G 63/78* (2013.01); *A61L 2300/604* (2013.01); *A61L 2430/32* (2013.01); *C08L 2203/02* (2013.01); *C08L 2203/18* (2013.01); *C08L 2205/02* (2013.01)

(56) References Cited

FOREIGN PATENT DOCUMENTS

| | | |
|---|---|---|
| JP | 2007-138131 A | 6/2007 |
| JP | 2008-037996 A | 2/2008 |
| JP | 2008-255349 A | 10/2008 |
| JP | 2016-190921 A | 11/2016 |
| JP | 2017-179234 A | 10/2017 |
| WO | 2019/035357 A1 | 2/2019 |

\* cited by examiner

POLYMER COMPOSITION, MOLDED BODY, AND NERVE REGENERATION INDUCING TUBE

TECHNICAL FIELD

This disclosure relates to a polymer composition containing polylactic acid and a dilactide/ε-caprolactone copolymer and a molded body thereof.

BACKGROUND

Polyesters produced from ester bond-forming monomers, represented by polylactic acid, polyglycolic acid, polycaprolactone, or copolymers thereof, are attracting attention as biodegradable or bioabsorbable polymers and are used in various fields including medical materials such as sutures, and sustained-release materials such as pharmaceuticals, agricultural chemicals, and fertilizers. Furthermore, they are also expected to serve as a packaging material such as a container and a film as a biodegradable general-purpose plastic.

However, in general, biodegradable polyesters and bioabsorbable polyesters produced from ester bond-forming monomers are fragile. Therefore, attempts have been made to develop various copolymers for the purpose of improving mechanical properties and obtaining a biodegradable polymer having practical strength and moldability.

For example, as a biodegradable/bioabsorbable polymer having a low Young's modulus and a high tensile strength, there has been proposed a polyester copolymer containing residues of two types of ester bond-forming monomers ("monomer A" and "monomer B") as main structural units in which an R value represented by the following formula is 0.45 or more and 0.99 or less and in which a degree of crystallization of at least one of monomer A residues and monomer B residues is less than 14% (see, for example, WO 2019/35857 A):

$$R = [AB]/(2[A][B]) \times 100$$

[A] is the molar fraction (%) of the monomer A residues in the polyester copolymer [B] is the molar fraction (%) of the monomer B residues in the polyester copolymer [AB] is the molar fraction (%) of the structure in which a monomer A residue and a monomer B residue are adjacent to each other in the polyester copolymer.

Attempts have also been made to improve mechanical properties by mixing biodegradable polymers. For example, as a composition having improved strength, flexibility, elongation percentage, tenacity, and the like, a biodegradable polymer blend (see, for example, Japanese Patent Laid-open Publication No. 2008-255349) containing at least one hard synthetic biodegradable polymer and at least one soft synthetic biodegradable polymer, having a higher strength and/or elongation than those of the hard or soft biodegradable polymer by themselves, and suitable for formation into at least one of a sheet or a film, a resin composition (see, for example, Japanese Patent Laid-open Publication No. 2017-179234) containing polylactic acid, an L-lactide/ε-caprolactone copolymer, and a filler, and the like have been proposed.

In general, it is known that polylactic acid and polyglycolic acid have high crystallinity and have high Young's moduli and are hard. However, molded bodies of those polymers have poor softness and are inferior in bio-followability required for medical materials. In addition, it has been reported that its hardness causes damage to surrounding tissues or protrusion accidents when embedded in the body.

Therefore, it has been studied to impart softness by copolymerizing polycaprolactone with those polymers. A multi-gradient polymer disclosed in WO '857 has a low Young's modulus and a high tensile strength and is thus easy to mold and difficult to break, and the polymer is suitable for a filler and a covering material. On the other hand, in applications such as a support and a fixing base material, in addition to these characteristics, ease of elastic deformation, that is, excellent flexibility, is required.

In addition, the resin composition described in JP '349 and JP '234 has a high Young's modulus, and a material having a low Young's modulus is required from the viewpoint of formability.

It could therefore be helpful to provide a polymer composition having a low Young's modulus, a high tensile strength, and excellent flexibility.

SUMMARY

We thus provide:

A polymer composition containing polylactic acid, and a dilactide/ε-caprolactone copolymer, in which a content of the polylactic acid relative to a total of 100 mass % of the polylactic acid and the dilactide/ε-caprolactone copolymer is 20 to 40 mass %, and in which the dilactide/ε-caprolactone copolymer satisfies (1) and (2):

(1) an R value represented by a following formula is 0.45 or more and 0.99 or less:

$$R = [AB]/(2[A][B]) \times 100$$

where

[A] is a molar fraction (%) of a dilactide residue in the dilactide/ε-caprolactone copolymer,

[B] is a molar fraction (%) of an ε-caprolactone residue in the dilactide/ε-caprolactone copolymer, and

[AB] is a molar fraction (%) of a structure in which a dilactide residue and an ε-caprolactone residue are adjacent to each other (A-B and B-A) in the dilactide/ε-caprolactone copolymer, and (2) at least one of the dilactide residue and the ε-caprolactone residue has a degree of crystallization of less than 14%.

A molded body made of the polymer composition.

A nerve regeneration inducing tube at least partially including the polymer composition.

A polymer composition having a low Young's modulus, a high tensile strength, and excellent flexibility is thus obtained.

DESCRIPTION OF REFERENCE SIGNS

E: Elongation
F: Tensile force (N)

DETAILED DESCRIPTION

Polylactic Acid

Polylactic acid in the polymer composition is a polymer obtained by polymerizing lactic acid by ester bonds. The polylactic acid may be a copolymer containing a component other than lactic acid, but the molar fraction of lactic acid in the polylactic acid is preferably 80% or more, more preferably 90% or more, still more preferably 100% to increase the crystallinity of lactic acid. There are two types of lactic acid, L-lactic acid and D-lactic acid, but a homopolymer of L-lactic acid is preferable from the viewpoint of biocompatibility in medical applications.

The weight average molecular weight of the polylactic acid is preferably 60,000 or more from the viewpoint of making the molecular chain difficult to unravel and further improving flexibility. Furthermore, 110,000 or more is more preferable from the viewpoint of further improving the tensile strength. On the other hand, the weight average molecular weight of the polylactic acid is preferably 200,000 or less so that the Young's modulus of the polymer composition will not increase due to excessive crystallization. The weight average molecular weight of the polylactic acid refers to a value in terms of polystyrene and can be measured by gel permeation chromatography (GP).

Method of Producing Polylactic Acid

The polylactic acid can be obtained by polymerizing or copolymerizing lactic acids such as L-lactic acid and $_D$-lactic acid. The polylactic acid can be synthesized, for example, by ring-opening polymerization of dilactide. The following describes an example of a method of synthesizing polylactic acid using $_L$-dilactide.

First, $_L$-dilactide and a co-initiator are collected in a separable flask. Examples of the co-initiator include lauryl alcohol.

Next, a catalyst is added under a nitrogen atmosphere, and the mixture is stirred while being heated so that the raw material is uniformly dissolved or melted. Examples of the catalyst include tin(II) octylate. The heating temperature is preferably from the viewpoint of uniformly dissolving the raw materials and, on the other hand, preferably 140° C. or lower from the viewpoint of suppressing volatilization of the raw materials. The stirring speed is preferably 80 rpm or more and 200 rpm or less. The heating time is preferably 10 minutes or more and 60 minutes or less.

The mixture is further heated and allowed to stand for 1 hour, the temperature is then lowered, and the mixture is further allowed to stand. The heating temperature at this time is preferably 150° C. or more and 180° C. or less. The standing time is preferably 2 hours or less from the viewpoint of suppressing excessive polymerization. The temperature when the temperature is lowered is preferably 120° C. or higher from the viewpoint of allowing the reaction to proceed and, on the other hand, is preferably 140° C. or lower from the viewpoint of suppressing volatilization of L-dilactide. The standing time is preferably 24 hours or less.

Thereafter, the inside of the flask is brought into a reduced pressure state while the temperature is maintained, and unreacted L-dilactide is removed. Finally, the reaction mixture is dissolved in chloroform or the like and added dropwise to methanol being stirred to precipitate polylactic acid. The stirring speed of methanol is preferably 200 rpm or more and 300 rpm or less. It is preferable to perform drying to remove the solvent in the obtained polylactic acid. The drying time is preferably 12 hours or more.

Dilactide/ε-Caprolactone Copolymer

A dilactide/ε-caprolactone copolymer in the polymer composition satisfies (1) and (2).

(1) An R value represented by a following formula is 0.45 or more and 0.99 or less:

$$R = [AB]/(2[A][B]) \times 100$$

where

[A] is a molar fraction (%) of a dilactide residue in the dilactide/ε-caprolactone copolymer,

[B] is a molar fraction (%) of an ε-caprolactone residue in the dilactide/ε-caprolactone copolymer, and

[AB] is a molar fraction (%) of a structure in which a dilactide residue and an ε-caprolactone residue are adjacent to each other (A-B and B-A) in the dilactide/ε-caprolactone copolymer.

The R value can be determined by quantifying the ratio of combinations of two adjacent monomers (A-A, B-B, A-B, and B-A) by nuclear magnetic resonance (NMR) measurement. Specifically, the dilactide/ε-caprolactone copolymer is dissolved in deuterated chloroform, and the ratio of the dilactide residues to the ε-caprolactone residues in the dilactide/ε-caprolactone copolymer is calculated by $^1$H-NMR analysis. In addition, regarding the methine group of dilactide (around 5.10 ppm), the α-methylene group of ε-caprolactone (around 2.35 ppm), and the ε-methylene group (around 4.10 ppm), adjacent monomer residues are separated by a signal derived from lactide or ε-caprolactone by $^1$H homo-spin decoupling, and each peak area is quantified. From each area ratio, [AB] of Formula 1 is calculated to calculate the R value. [AB] is the molar fraction (%) of a structure in which the dilactide residue and the ε-caprolactone residue are adjacent to each other and specifically is the ratio of the number of A-B and B-A to the total number of A-A, A-B, B-A, and B-B.

The R value is used as an index indicating the randomness of the sequence of monomer residues in the dilactide/ε-caprolactone copolymer. For example, in a random copolymer having a completely random monomer sequence, the R value is 1. When the R value is 0.45 or more, crystallinity is low, and softness is excellent. The R value is preferably 0.50 or more. On the other hand, when the R value is 0.99 or less, adhesiveness can be suppressed. The R value is preferably 0.80 or less.

(2) At least one of the dilactide residue and the ε-caprolactone residue has a degree of crystallization of less than 14%.

When the degree of crystallization is less than 14%, a polyester copolymer suitable for medical materials and elastomer applications can be obtained by reducing the Young's modulus to provide softness. The degree of crystallization of the dilactide residues is preferably less than 14%, more preferably 10% or less.

The degree of crystallization of monomer residues as used herein is the ratio of the heat of fusion per unit mass of a certain type of monomer residues in the dilactide/ε-caprolactone copolymer to the product of the heat of fusion per unit mass of a homopolymer composed of only the monomer residues and the mass fraction of the monomer residues in the dilactide/ε-caprolactone copolymer. That is, the degree of crystallization of the dilactide residues is the ratio of the heat of fusion per unit mass of the dilactide residue residues in the dilactide/ε-caprolactone copolymer to the product of the heat of fusion per unit mass of a homopolymer composed only of dilactide and the mass fraction of the dilactide residue residues in the dilactide/ε-caprolactone copolymer. The degrees of crystallization of the dilactide residues and the ε-caprolactone residues each indicate a ratio of the dilactide residues or the ε-caprolactone residues having a crystal structure in the dilactide/ε-caprolactone copolymer. The degree of crystallization can be measured by DSC using a differential scanning calorimeter.

The dilactide/ε-caprolactone copolymer may be linear or branched.

The weight average molecular weight of the dilactide/ε-caprolactone copolymer is preferably 60,000 or more, more preferably 100,000 or more, from the viewpoint of further reducing the Young's modulus of the polymer composition and further improving the tensile strength. On the other hand, the weight average molecular weight of the dilactide/ε-caprolactone copolymer is preferably 400,000 or less from the viewpoint of the viscosity and solubility of the polymer composition described later. The weight average molecular weight of the dilactide/ε-caprolactone copolymer refers to a value in terms of polystyrene and can be measured by gel permeation chromatography (GPC).

The dilactide/ε-caprolactone copolymer preferably has a gradient structure in which dilactide residues and ε-caprolactone residues form a composition gradient in the skeleton.

The gradient structure having a composition gradient in the skeleton refers to a structure in which the composition of monomer residues continuously changes from the polymerization initiation end to the polymerization termination end along the molecular chain.

Schematically, for example, the residue A and the residue B are arranged like AAAAABAAABAABBABABBBBA-BBBB.

Since the dilactide/ε-caprolactone copolymer has a gradient structure in which the dilactide residues and the ε-caprolactone residues form a composition gradient in the skeleton, the crystallinity can be reduced, and softness can be provided, as compared to a block copolymer structure.

The randomness of the distribution of the monomer residues constituting the dilactide/ε-caprolactone copolymer varies depending on the reactivity of the monomers during polymerization. That is, when one of the monomers of dilactide and caprolactone is bonded to the same type of monomer and the other type of monomer with the same probability during polymerization, a random copolymer in which monomer residues are completely randomly distributed is obtained. However, when one monomer tends to be easily bonded to a certain monomer, a gradient copolymer having a biased distribution of monomer residues is obtained.

The reactivity is greatly different between dilactide and ε-caprolactone as described in D. W. Grijpma et al., Polymer Bulletin, 25,335,341, and dilactide has a higher initial polymerization rate than ε-caprolactone. An initial polymerization rate $V_A$ of dilactide is 3.6%/h in terms of reaction rate (%), and an initial polymerization rate $V_B$ of ε-caprolactone is 0.88%/h. When dilactide and ε-caprolactone are copolymerized, dilactide is easily bonded to dilactide. Therefore, a gradient structure in which the proportion of the dilactide units gradually decreases from the polymerization initiation end to the polymerization termination end is formed.

That is, according to a copolymerization method in which monomers of dilactide and ε-caprolactone are mixed and allowed to react, in general, the dilactide/ε-caprolactone copolymer easily forms a gradient structure over the entire skeleton of the polymer.

Furthermore, the dilactide/ε-caprolactone copolymer has a gradient structure in units of macromers and preferably has a structure in which two or more macromer units are linked.

The "macromer" means a high molecular weight compound having a polymerizable functional group, and in a polymer, the macromer unit constitutes a part of the skeleton of the polymer. In a structure in which two or more macromer units having a gradient structure are linked, an arrangement such as (AAABAABBABBB)·(AAABAAB-BABBB) is formed.

A macromer having a gradient structure is also referred to as a "gradient macromer," and a unit of the gradient macromer in the polymer is also referred to as a "gradient macromer unit."

With the structure in which two or more gradient macromer units are linked, it is possible to effectively obtain a dilactide/ε-caprolactone copolymer with controlled randomness as in (1) described above, and it is possible to obtain a dilactide/ε-caprolactone copolymer with effectively reduced crystallinity as in (2) described above, even when the degree of polymerization is increased. Therefore, preferably, a polymer composition having a low Young's modulus and a high tensile strength can be effectively obtained.

The number of macromer units in the structure in which macromer units are linked is preferably 3 or more, more preferably 6 or more, from the viewpoint of further enhancing the tensile strength. On the other hand, from the viewpoint of moderately reducing the viscosity and improving the handleability, the number of linked macromer units is preferably 20 or less.

A structure in which two or more gradient macromer units are linked is also referred to as a "multi-gradient structure," and a copolymer having a multi-gradient structure is also referred to as a "multi-gradient copolymer."

The maximum point stress when the dilactide/ε-caprolactone copolymer is formed into a film is preferably 5 MPa or more and 30 MPa or less, which is about equal to the maximum point stress of a biological tissue. In addition, the Young's modulus of the dilactide/ε-caprolactone copolymer is preferably 1.0 MPa or more and 6.3 MPa or less, which is about equal to the Young's modulus of a biological tissue.

The maximum point stress and Young's modulus when the dilactide/ε-caprolactone copolymer is formed into a film can be measured in accordance with a method defined in JIS K 6251 (2017). Specifically, a solution obtained by drying a copolymer of dilactide/ε-caprolactone under reduced pressure and dissolving the product in chloroform to achieve a concentration of 5 mass % is transferred onto a petri dish made of "Teflon" (registered trademark) and dried at normal pressure and room temperature for one day and night. A polymer film having a thickness of 0.1 mm obtained by drying the product under reduced pressure is cut into a strip shape (30 mm×5 mm), and the maximum point stress and the Young's modulus are measured by performing a tensile test under the following conditions using a small desktop tester EZ-LX (manufactured by Shimadzu Corporation):
Initial length: 10 mm,
Tensile speed: 500 mm/min, and
Load cell: 50 N.

The maximum point stress and the Young's modulus of the copolymer of dilactide/ε-caprolactone can be determined by performing measurement three times each and calculating the number average value.

Setting the maximum point stress and Young's modulus of the dilactide/ε-caprolactone copolymer within the above ranges can be effectively achieved by forming a structure in which two or more gradient macromer units are linked by a production method including a multimerization step described later.

Method of Producing Dilactide/ε-Caprolactone Copolymer

As an example, a production method of the dilactide/ε-caprolactone copolymer includes:

a macromer synthesis step of blending and polymerizing dilactide and ε-caprolactone such that the sum of the dilactide residue and the ε-caprolactone residue is 50 mol % or more of the whole residues and such that each of the dilactide residue and the ε-caprolactone residue is 20 mol % or more of the whole residues at the completion of polymerization; and a multimerization step of linking the macromers obtained in the macromer synthesis step or additionally adding dilactide and ε-caprolactone to the macromer solution obtained in the macromer synthesis step to perform multimerization.

Macromer Synthesis Step

In the macromer synthesis step, dilactide and ε-caprolactone are blended such that the sum of the dilactide residues and the ε-caprolactone residues is 50 mol % or more of the whole residues and such that the dilactide residues and the ε-caprolactone residues are each 20 mol % or more of the whole residues at the completion of polymerization in theory, and polymerization is performed. As a result, a dilactide/ε-caprolactone copolymer containing dilactide residues and ε-caprolactone residues as main structural units is obtained, but in the method, since the multimerization step described later is further performed, the dilactide/ε-caprolactone copolymer obtained in this step is referred to as a "macromer."

In this step, a macromer having a gradient structure in which the dilactide residues and the ε-caprolactone residues form a composition gradient in the skeleton is obtained because of the difference in initial polymerization rates between dilactide and ε-caprolactone.

In the macromer synthesis step, to realize such a gradient structure, it is desirable to synthesize the macromer by a polymerization reaction occurring in one direction from the initiation end. Preferable examples of such a synthesis reaction include ring-opening polymerization and living polymerization.

An example of the method of synthesizing a lactide/caprolactone macromer will be described more specifically. First, dilactide, ε-caprolactone, and a catalyst are placed in a reaction vessel equipped with a stirrer and stirred while being heated under a nitrogen stream. It is preferable to perform heating and stirring in the reaction vessel under reduced pressure to remove moisture in the reaction vessel.

As the stirrer, a stirrer equipped with a propeller-type stirring blade is preferable, and the rotation speed of the stirring blade is preferably 50 rpm or more and 200 rpm or less.

The heating temperature in the polymerization reaction is preferably 100° C. or higher and 250° C. or lower. The reaction time of the polymerization reaction is preferably 3 hours or more, more preferably 5 hours or more, still more preferably 7 hours or more, from the viewpoint of increasing the degree of polymerization. On the other hand, the reaction time of the polymerization reaction is preferably 24 hours or less from the viewpoint of further improving productivity.

It is preferable that dilactide and ε-caprolactone are used after being purified in advance to remove impurities.

Examples of the catalyst include tin octylate, antimony trifluoride, zinc powder, dibutyltin oxide, and tin oxalate. Examples of the method of adding the catalyst to the reaction system include a method in which the catalyst is added such that the catalyst is dispersed in the raw materials at the time of charging the raw materials and a method in which the catalyst is added in a dispersed state in a medium at the time of starting the pressure reduction or immediately before starting the heating in the above-described method. The amount of the catalyst used is preferably 0.01 parts by mass or more, more preferably 0.04 parts by mass or more, in terms of metal atoms with respect to a total of 100 parts by mass of dilactide and ε-caprolactone from the viewpoint of shortening the reaction time and further improving the productivity. On the other hand, the amount of the catalyst used is preferably 0.5 parts by mass or less in terms of metal atoms with respect to the total amount of dilactide and ε-caprolactone from the viewpoint of further reducing the amount of metal remaining in the dilactide/ε-caprolactone copolymer.

When water is used as a co-initiator, it is preferable to perform a cocatalyst reaction at around 90° C. prior to the polymerization reaction.

The macromer obtained in this step preferably has an R value similar to that of the dilactide/ε-caprolactone copolymer described in the above (1), that is, an R value represented by the following formula of 0.45 or more and 0.99 or less, more preferably 0.50 or more and 0.80 or less, $$R \text{ value} = [AB]/(2[A][B]) \times 100$$

[A] is the mole fraction (%) of dilactide residues in the macromer,
[B] is the mole fraction (%) of ε-caprolactone residues in the macromer, and
[AB] is the molar fraction (%) of a structure in which a dilactide residue and an ε-caprolactone residue are adjacent to each other (A-B and B-A) in the macromer to facilitate the production of the dilactide/ε-caprolactone copolymer that finally satisfies the R value shown in the above (1).

Similarly, the macromer obtained in this step has the degree of crystallization of the monomer residues described in the above (2), that is, the degree of crystallization of at least one of the dilactide residues and the ε-caprolactone residues is preferably less than 14%, more preferably 10% or less, still more preferably 5% or less, and most preferably 1% or less to facilitate the production of the dilactide/ε-caprolactone copolymer finally having the degree of crystallization of the dilactide residues or the ε-caprolactone residues shown in the above (2).

The weight average molecular weight of the macromer synthesized in the macromer synthesis step is preferably 10,000 or more, more preferably 20,000 or more. In addition, to further reduce the crystallinity and further improve the softness, it is preferably 150,000 or less, more preferably 100,000 or less.

Multimerization Step

In the multimerization step, the macromers obtained in the macromer synthesis step are linked to each other, or dilactide and caprolactone are additionally added to the macromer solution obtained in the macromer synthesis step to perform multimerization. In this step, the macromers obtained in one macromer synthesis step may be linked to each other, or a plurality of macromers obtained in two or more macromer synthesis steps may be linked to each other. The term "multimerization" means that the dilactide residues and the caprolactone residues form a structure in which a plurality of molecular chains having a gradient structure having a composition gradient in the skeleton are repeated by any one of these methods.

The number of linked macromer units can be adjusted with the catalyst used in the multimerization step and the reaction time. When multimerization is performed by linking macromers, the number of macromer units can be determined by dividing the weight average molecular weight of the finally obtained dilactide/ε-caprolactone copolymer by the weight average molecular weight of the macromer.

The reaction temperature in the condensation reaction in the multimerization step is preferably 20° C. or higher from the viewpoint of efficiently promoting the condensation reaction. On the other hand, the reaction temperature of the condensation reaction is preferably 50° C. or lower from the viewpoint of suppressing volatilization of the solvent. The reaction time in the condensation reaction is preferably 15 hours or more from the viewpoint of setting the number of macromer units to be multimerized to the above-mentioned preferable range. On the other hand, the reaction time of the condensation reaction is preferably 24 hours or less from the viewpoint of narrowing the molecular weight distribution.

In producing a linear dilactide/ε-caprolactone copolymer, for example, it can be synthesized by bonding similar gradient macromers to both ends of the gradient macromer one molecule at a time via the ends.

When the gradient macromer has a hydroxy group and a carboxy group at respective ends, the ends are condensed with a condensing agent to provide a multimerized dilactide/ε-caprolactone copolymer. Examples of the condensing agent include 4,4-dimethylaminopyridinium p-toluenesulfonate, N,N'-dicyclohexylcarbodiimide, N,N'-diisopropylcarbodiimide, and N,N'-carbonyldiimidazole. Two or more of these compounds may be used.

In addition, when the polymerization reaction is living, that is, when the polymerization reaction can be continuously started from the end of the polymer, multimerization can be performed by repeating an operation of additionally adding dilactide and ε-caprolactone to the gradient macromer solution after the completion of the polymerization reaction.

Alternatively, the gradient macromers may be multimerized via a linker as long as the dynamic characteristics of the polymer are not affected. In particular, when a linker containing a plurality of carboxy groups and/or a plurality of hydroxy groups such as 2,2-bis(hydroxymethyl)propionic acid, is used, a branched polyester copolymer in which the linker serves as a branch point can be synthesized.

The dilactide/ε-caprolactone copolymer obtained by the production method as described above is a copolymer having a structure in which two or more macromer units each including didilactide residues and caprolactone residues having a composition gradient in the skeleton of are linked, and this is a preferred aspect of the dilactide/ε-caprolactone copolymer.

Polymer Composition

The polymer composition contains the above-described polylactic acid and the dilactide/ε-caprolactone copolymer.

The dilactide/ε-caprolactone satisfying the above (1) and (2) has a low degree of crystallization, a reduced Young's modulus, and an improved tensile strength but is in a state in which the molecular chains are merely entangled with each other. Therefore, the dilactide/ε-caprolactone is first deformed so that the entanglement between the molecular chains is alleviated when the dilactide/ε-caprolactone is subjected to stress, an elastic force is hardly generated, and the dilactide/ε-caprolactone has low flexibility at the initial stage of elongation. On the other hand, it is considered that polylactic acid has high crystallinity and forms a crystal structure with the dilactide residue in the dilactide/ε-caprolactone copolymer. It is considered that, due to such a crystal structure, a crosslinking point is formed between molecular chains of the dilactide/ε-caprolactone copolymer, an elastic force like rubber is exerted when stress is applied, and flexibility can be improved.

The polymer composition is required to contain 20 to 40 mass % of polylactic acid with respect to a total of 100 mass % of the polylactic acid and the dilactide/ε-caprolactone copolymer. When the content of the polylactic acid is 20 mass % or more, more preferably 30 mass % or more, crystal formation of the polylactic acid and the dilactide residues is made sufficient, and flexibility can be improved. On the other hand, by setting the content of the polylactic acid to 40 mass % or less, more preferably 35 mass % or less, excessive crystallization of the polylactic acid and dilactide can be suppressed, and an increase in Young's modulus and a decrease in tensile strength can be prevented.

The maximum point stress when the polymer composition is formed into a film is preferably 5 MPa or more and 30 MPa or less, which is about equal to the maximum point stress of a biological tissue. In addition, the Young's modulus is preferably 1.0 MPa or more and 6.3 MPa or less, which is about equal to the Young's modulus of a biological tissue.

The maximum point stress and Young's modulus when the polymer composition is formed into a film can be measured in accordance with a method defined in JIS K 6251 (2017), and the details are similar to those in the dilactide/ε-caprolactone copolymer.

Method of Producing Polymer Composition

The polymer composition can be obtained, for example, by stirring the above-described polylactic acid and dilactide/ε-caprolactone copolymer in a molten state or a solution state. From the viewpoint of suppressing thermal decomposition, stirring is preferably performed in a solution state. It is more preferable to put the polymers constituting the polymer composition together in the same solvent, dissolve the polymers with stirring, and then volatilize and remove the solvent.

Molded Body Made of Polymer Composition

The polymer composition is excellent in flexibility and can therefore be used for a molded body for use involving frequent deformation. In particular, even when the molded body is transplanted into a body as a medical molded body, the molded body has softness to follow the deformation of the body, exhibits resistance to deformation of a certain level or more, and can also serve as a support. In particular, application to a nerve regeneration inducing tube that requires such a function is preferable.

EXAMPLES

Our compositions, molded bodies, tubes and methods will be described below with reference to specific examples, but this disclosure should not be construed as limited to these examples, and all technical aspects that those skilled in the art would consider being implementable and specific aspects thereof should be understood as being included in this disclosure.

Measurement Method (1) Measurement of the Weight Average Molecular Weight by Gel Permeation Chromatography (GPC)

A dilactide/ε-caprolactone copolymer or polylactic acid to be measured was dissolved in chloroform and allowed to pass through a 0.45 μm syringe filter (DISMIC-13HP; manufactured by ADVANTEC) to remove impurities and the like. Then, the weight average molecular weights of the dilactide/ε-caprolactone copolymer and the polylactic acid in terms of polystyrene were calculated on the basis of GPC measurement under the following conditions:

Device name: Prominence (manufactured by Shimadzu Corporation)
Mobile phase: Chloroform (for HPLC) (manufactured by Wako Pure Chemical Industries, Ltd.)
Flow rate: 1 mL/min
Column: TSKgel GMHHR-M (φ7.8 mm×300 mm; manufactured by Tosoh Corporation)
Detector: A UV detector (254 nm) and an RI detector were activated, and the results from the RI detector were used for the calculation of the weight average molecular weight
Column and detector temperatures: 35° C.
Standard substance: polystyrene.

(2) Measurement of the Degree of Crystallization of Dilactide Residues by Differential Scanning Calorimetry (DSC)

The dilactide/ε-caprolactone copolymer to be measured was collected in an aluminum pan, and the heat of fusion was calculated on the basis of DSC using a differential scanning calorimeter (EXTAR 6000; manufactured by Seiko Instruments Inc.) under the following conditions. From the obtained value of the heat of fusion, the degree of crystallization was calculated by the following formula:

Degree of crystallization=(heat of fusion of dilactide/ε-caprolactone copolymer per unit mass of dilactide residues)/{(heat of fusion per unit mass of homopolymer composed only of dilactide residues)×(mass fraction of dilactide residues in dilactide/ε-caprolactone copolymer)}×100

Device name: EXSTAR 6000 (manufactured by Seiko Instruments Inc.)
Temperature conditions: 25° C.→temperature increase to 250° C. at 10° C./min→temperature retention for 5 min at 250° C.→temperature decrease to −70° C. at 10° C./min→temperature increase to 250° C. at 10° C./min→temperature retention for 5 min at 250° C.→temperature decrease to 25° C. at 100° C./min in this order
Reference material: aluminum.

(3) Measurement of the Molar Fraction (%) and R Value of Each Residue by Nuclear Magnetic Resonance (NMR)

The dilactide/ε-caprolactone copolymer to be measured was dissolved in deuterated chloroform, and the ratio of the dilactide residues to the caprolactone residues in the dilactide/ε-caprolactone copolymer was calculated by $^1$H-NMR under the following conditions. In addition, the methine group of lactide (around 5.10 ppm), the α-methylene group of caprolactone (around 2.35 ppm), and the ε-methylene group (around 4.10 ppm) were separated on the basis of a signal derived from an adjacent monomer residue, lactide or caprolactone, by $^1$H homo-spin decoupling, and each peak area was quantified. From each area ratio, [AB] of Formula 1 was calculated to calculate the R value. [AB] is the molar fraction (%) of a structure in which the dilactide residue and the caprolactone residue are adjacent to each other and specifically is the ratio of the number of A-B and B-A to the total number of A-A, A-B, BA, and B-B.

Device name: JNM-EX270 (manufactured by JEOL Ltd.)
$^1$H homo-spin decoupling irradiation position: 1.66 ppm
Solvent: deuterated chloroform
Measurement temperature: room temperature (4) Measurement of the Young's Modulus and Maximum Point Stress by Tensile Test A solution obtained by drying a dilactide/ε-caprolactone copolymer or a polymer composition solution obtained in each of the Examples and Comparative Examples under reduced pressure and dissolving the product in chloroform to achieve a concentration of 5 wt % was transferred onto a petri dish made of "Teflon" (registered trademark) and dried at normal pressure and room temperature for one day and night. The product was dried under reduced pressure to provide a polymer composition film.

The obtained film (thickness: about 0.1 mm) was cut into a strip shape (50 mm×5 mm), and a tensile test was conducted under the following conditions in accordance with JIS K 6251 (2017) using EZ-LX (manufactured by Shimadzu Corporation) to calculate the Young's modulus and the maximum point stress. The measurement conditions in JIS K 6251 applied mutatis mutandis are common to the 2017 edition and the 2010 edition.

Device name: EZ-LX (manufactured by Shimadzu Corporation)
Initial length: 10 mm
Tensile speed: 500 mm/min
Load cell: 50 N
Number of tests: 3 times (5) Evaluation of Flexibility In the extension-stress curve (FIGS. 1 to 9) obtained by performing a tensile test by the method described in the above (4) using the polymer composition solution or the polymer solution obtained in each of the Examples and Comparative Examples, the stress until the elongation at which the maximum point stress was observed was approximated by a linear equation (Y=aX, where Y is stress, X is extension, and a is a constant), and a coefficient $r^2$ of determination was calculated from the average value obtained by tests repeated three times. Since flexibility is the ease of elastic deformation, it means that the closer the value of the coefficient $r^2$ of determination is to 1, the easier the elastic deformation is, and a coefficient of determination of 0.85 or more is an indication of excellent flexibility.

Synthesis Example 1: Synthesis of Dilactide/ε-Caprolactone Copolymer

As monomers, 25 g of L-dilactide (manufactured by Corbion N.V.) and 18.3 mL of ε-caprolactone (manufactured by Wako Pure Chemical Industries, Ltd.) were collected in a separable flask. Under a nitrogen atmosphere, a solution in which 0.05 parts by mass (in terms of tin) of tin(II) octylate (manufactured by Wako Pure Chemical Industries, Ltd.) as a catalyst with respect to a total of 100 parts by mass of dilactide and ε-caprolactone was dissolved in 3.5 mL of toluene (super dehydrated) (manufactured by Wako Pure Chemical Industries, Ltd.) and 227.4 mg of hydroxypivalic acid (manufactured by Tokyo Chemical Industry Co., Ltd.) as a co-initiator were added, and the mixture was stirred at a stirring speed of 100 rpm for 12 hours while being heated to 140° C. and subjected to a copolymerization reaction to provide a macromer solution.

To the resulting macromer solution were added 1.67 g of 4,4-dimethylaminopyridinium p-toluenesulfonate (synthetic product) as a catalyst and 617.9 mg of 4,4-dimethylaminopyridine (manufactured by Wako Pure Chemical Industries, Ltd.). These were dissolved in 255 mL of dichloromethane (dehydrated) (manufactured by Wako Pure Chemical Industries, Ltd.) under a nitrogen atmosphere, 5.76 g of dicyclohexylcarbodiimide (manufactured by Sigma-Aldrich Co. LLC.) was added as a condensing agent, and the mixture was stirred at 25° C. and a stirring speed of 100 rpm for 18 hours to perform condensation polymerization.

To the reaction mixture, 3.0 mL of acetic acid (manufactured by Wako Pure Chemical Industries, Ltd.) and chloroform in such an amount that the concentration of a dilactide/ε-caprolactone copolymer would be 15 mass % were added, and the mixture was stirred at 25° C. and a stirring speed of 200 rpm for 2 hours. Thereafter, the reaction mixture was added dropwise to 2.0 L of methanol with stirring at a stirring speed of 300 rpm to provide a precipitate. The obtained precipitate was dried for 18 hours to provide a dilactide/ε-caprolactone copolymer having a multi-gradient structure. The obtained dilactide/ε-caprolactone copolymer had a weight average molecular weight of 240,000, a degree of polymerization of a macromonomer unit of 7.1, a degree of crystallization of dilactide residues of 0.0%, a degree of crystallization of ε-caprolactone residues of 0.0%, a molar fraction of dilactide residues of 52%, a molar fraction of ε-caprolactone residues of 48%, a molar fraction of a structure in which a dilactide residue and an ε-caprolactone residue were adjacent to each other of 30%, an R value of 0.60, a Young's modulus of 3.9 MPa, and a maximum point stress of 22.2 MPa.

Synthesis Example 2: Synthesis of Dilactide/ε-Caprolactone Copolymer

In a separable flask, 50.0 g of L-lactide (PURASORB L; PURAC) and 36.6 mL of ε-caprolactone (manufactured by FUJIFILM Wako Pure Chemical Corporation) as monomers and 0.036 g of octanol as an initiator were collected.

The mixture was placed in an argon atmosphere, 0.27 g of tin(II) octylate (manufactured by FUJIFILM Wako Pure Chemical Corporation) that was a catalyst dissolved in 5.8 mL of toluene (super dehydrated) (manufactured by FUJIFILM Wako Pure Chemical Corporation) was added thereto, and the mixture was allowed to react at 140° C. and a stirring speed of 100 rpm for 24 hours to provide a crude polymer.

The obtained crude polymer was dissolved in 200 mL of chloroform and added dropwise to 3,000 mL of hexane being stirred to provide a precipitate. The precipitate was dried under reduced pressure at 50° C. for 18 hours to provide a dilactide/ε-caprolactone copolymer having a gradient structure. The obtained dilactide/ε-caprolactone copolymer had a weight average molecular weight of 200,000, a degree of crystallization of dilactide residues of 0.0%, a degree of crystallization of ε-caprolactone residues of 0.0%, a molar fraction of dilactide residues of 50%, a molar fraction of ε-caprolactone residues of 50%, a molar fraction of a structure in which a dilactide residue and an ε-caprolactone residue were adjacent to each other of 43.5%, an R value of 0.87, a Young's modulus of 0.76 MPa, and a maximum point stress of 16.6 MPa.

Example 1

Figure 1:
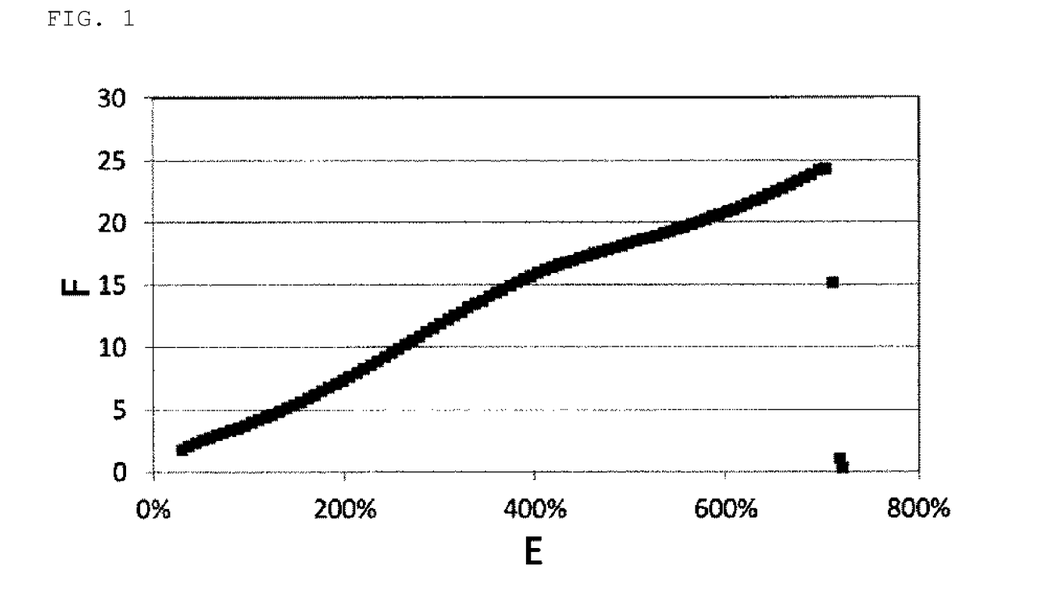
FIG. 1 is a graph of an extension-stress curve of a polymer composition obtained in Example 1.

In 30 mL of chloroform, 10 g of a mixture obtained by mixing the dilactide/ε-caprolactone copolymer obtained in Synthesis Example 1 and poly-L-lactic acid (manufactured by Corbion N.V.) (weight average molecular weight: 180,000) so that the mass ratio was dilactide/ε-caprolactone copolymer:polylactic acid=70:30 was dissolved to prepare a polymer composition solution. The results evaluated by the above-described method are shown in Table 1, and the extension-stress curve is shown in FIG. 1.

Comparative Example 1

Figure 2:
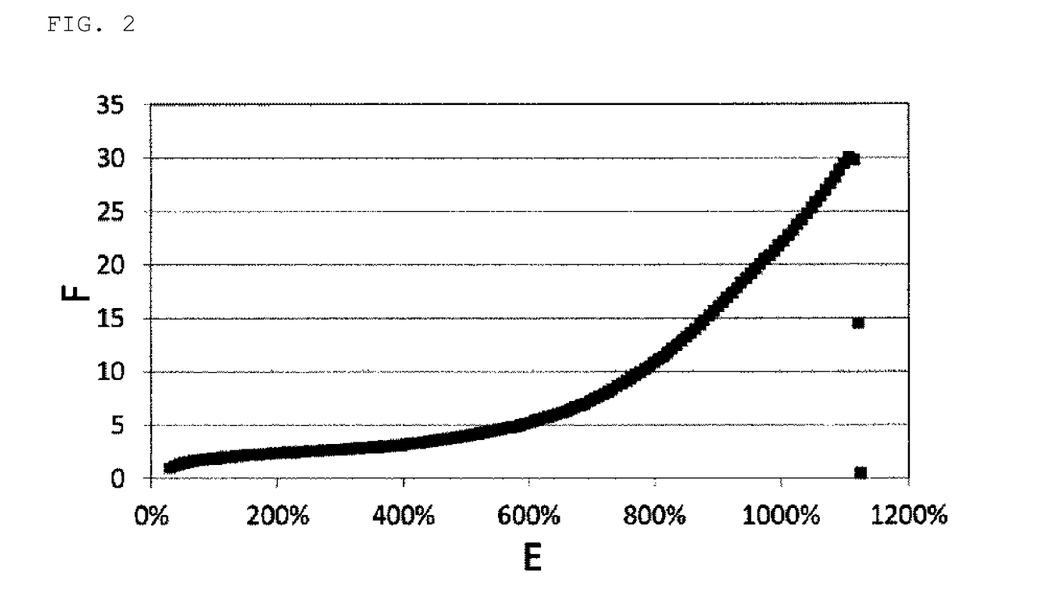
FIG. 2 is a graph of an extension-stress curve of a polymer composition obtained in Comparative Example 1.

In 30 mL of chloroform, 10 g of the dilactide/ε-caprolactone copolymer obtained in Synthesis Example 1 was dissolved to prepare a polymer solution. The results evaluated by the above-described method are shown in Table 1, and the extension-stress curve is shown in FIG. 2.

Comparative Example 2

Figure 3:
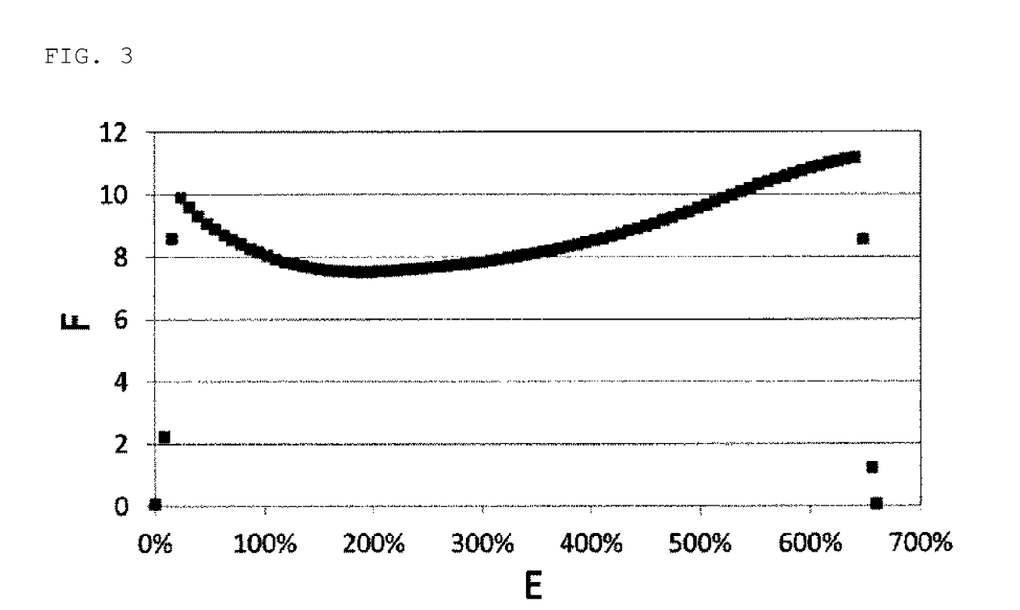
FIG. 3 is a graph of an extension-stress curve of a polymer composition obtained in Comparative Example 2.

A polymer composition solution was prepared in a similar manner to that in Example 1 except that the mass ratio of the dilactide/ε-caprolactone copolymer and the polylactic acid was changed to dilactide/ε-caprolactone copolymer:polylactic acid=50:50. The results evaluated by the above-described method are shown in Table 1, and the extension-stress curve is shown in FIG. 3.

Comparative Example 3

Figure 4:
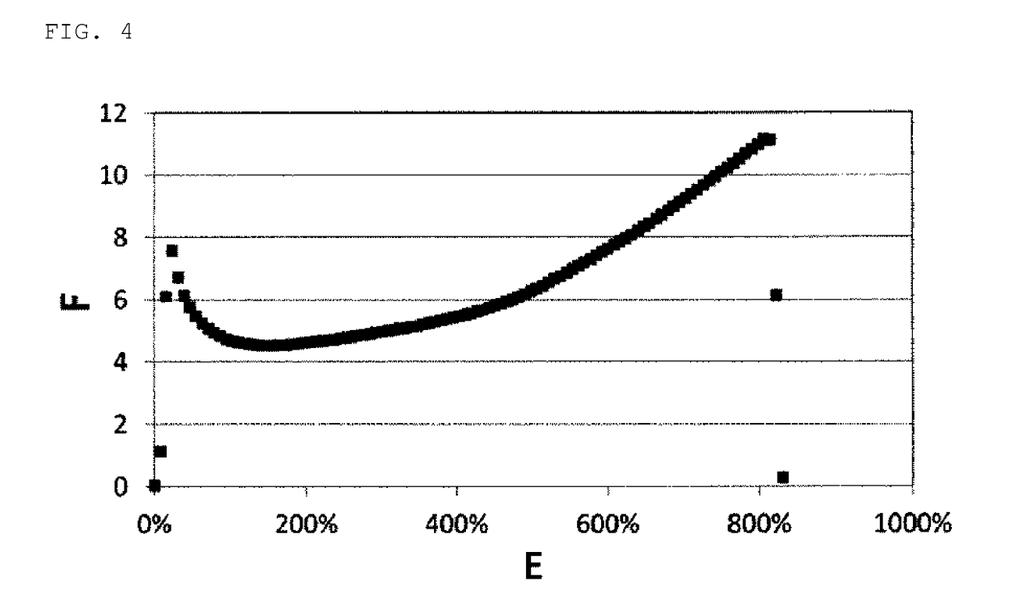
FIG. 4 is a graph of an extension-stress curve of a polymer composition obtained in Comparative Example 3.

A polymer composition solution was prepared in a similar manner to that in Example 1 except that the mass ratio of the dilactide/ε-caprolactone copolymer and the polylactic acid was changed to dilactide/ε-caprolactone copolymer:polylactic acid=30:70. The results evaluated by the above-described method are shown in Table 1, and the extension-stress curve is shown in FIG. 4.

Comparative Example 4

Figure 5:
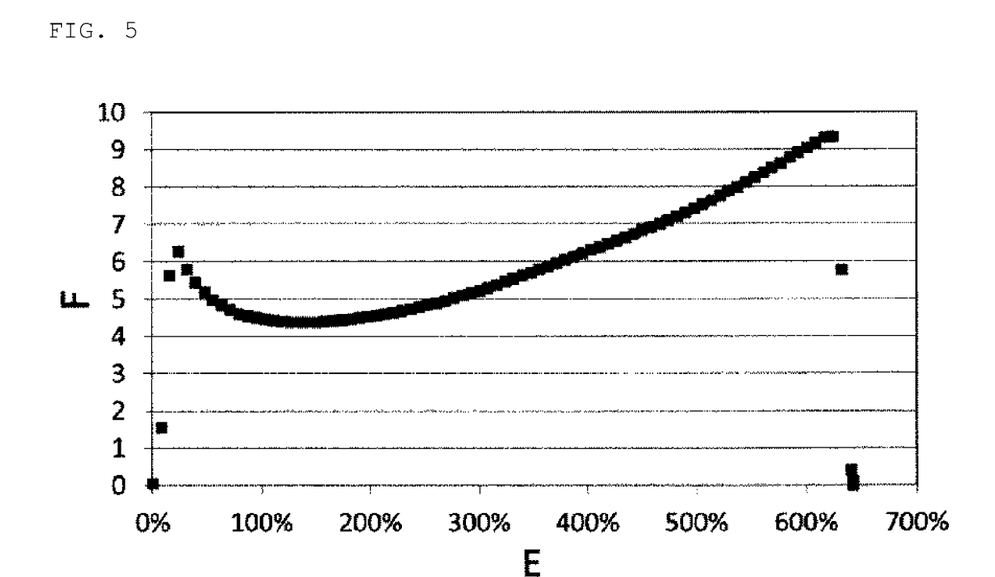
FIG. 5 is a graph of an extension-stress curve of a polymer obtained in Comparative Example 4.

In 30 mL of chloroform, 10 g of poly-L-lactic acid (manufactured by Corbion N.V.) was dissolved to prepare a polymer solution. The results evaluated by the above-described method are shown in Table 1, and the extension-stress curve is shown in FIG. 5.

Example 2

Figure 6:
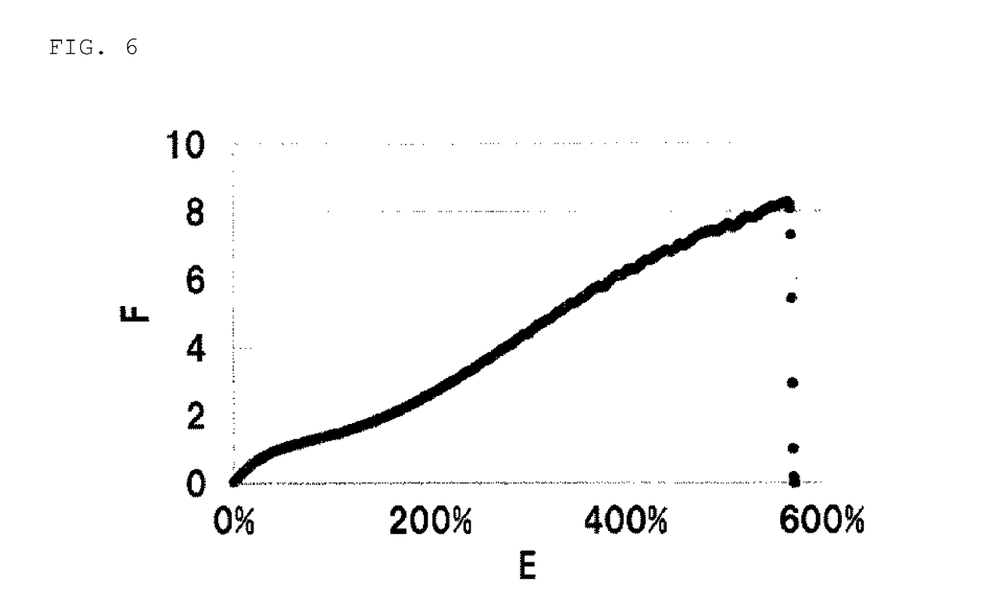
FIG. 6 is a graph of an extension-stress curve of a polymer composition obtained in Example 2.

A polymer composition solution was prepared in a similar manner to that in Example 1 except that the dilactide/ε-caprolactone copolymer was changed to that obtained in Synthesis Example 2. The results evaluated by the above-described method are shown in Table 1, and the extension-stress curve is shown in FIG. 6.

Example 3

Figure 7:
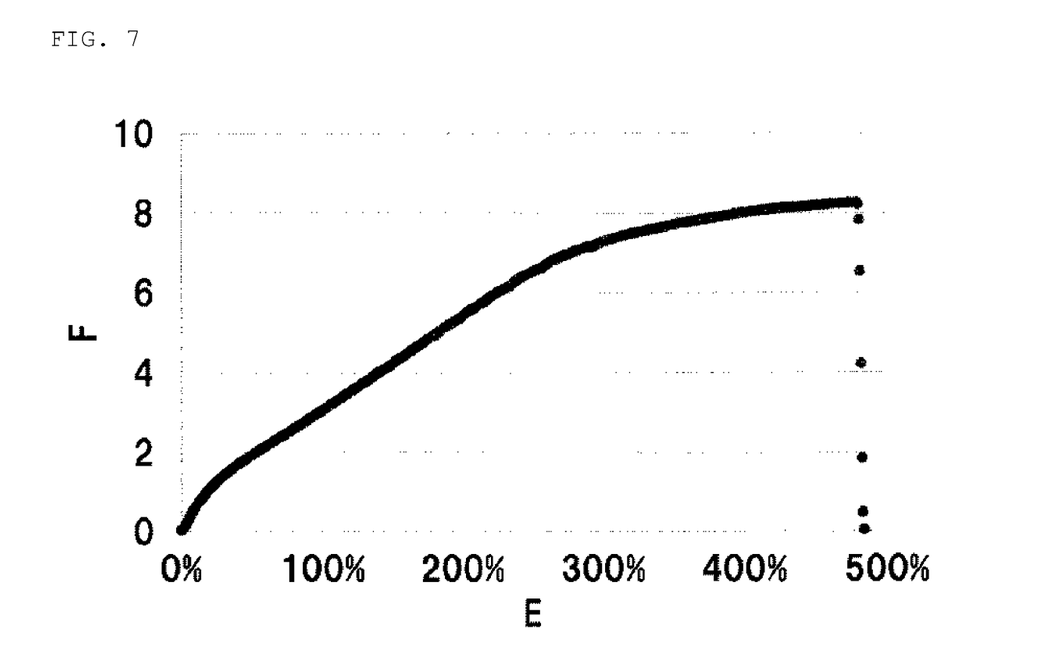
FIG. 7 is a graph of an extension-stress curve of a polymer composition obtained in Example 3.

A polymer composition solution was prepared in a similar manner to that in Example 2 except that the ratio of the dilactide/ε-caprolactone copolymer and the polylactic acid was changed to dilactide/ε-caprolactone copolymer:polylactic acid=60:40. The results evaluated by the above-described method are shown in Table 1, and the extension-stress curve is shown in FIG. 7.

Example 4

Figure 8:
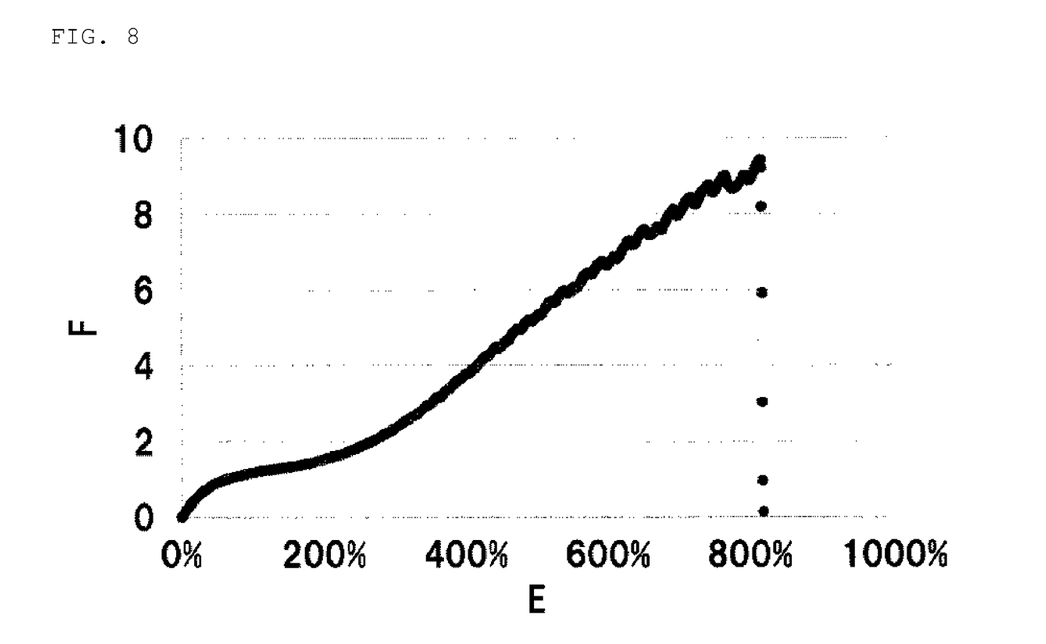
FIG. 8 is a graph of an extension-stress curve of a polymer composition obtained in Example 4.

A polymer composition solution was prepared in a similar manner to that in Example 2 except that the ratio of the dilactide/ε-caprolactone copolymer and the polylactic acid was changed to dilactide/ε-caprolactone copolymer:polylactic acid=80:20. The results evaluated by the above-described method are shown in Table 1, and the extension-stress curve is shown in FIG. 8.

Comparative Example 5

Figure 9:
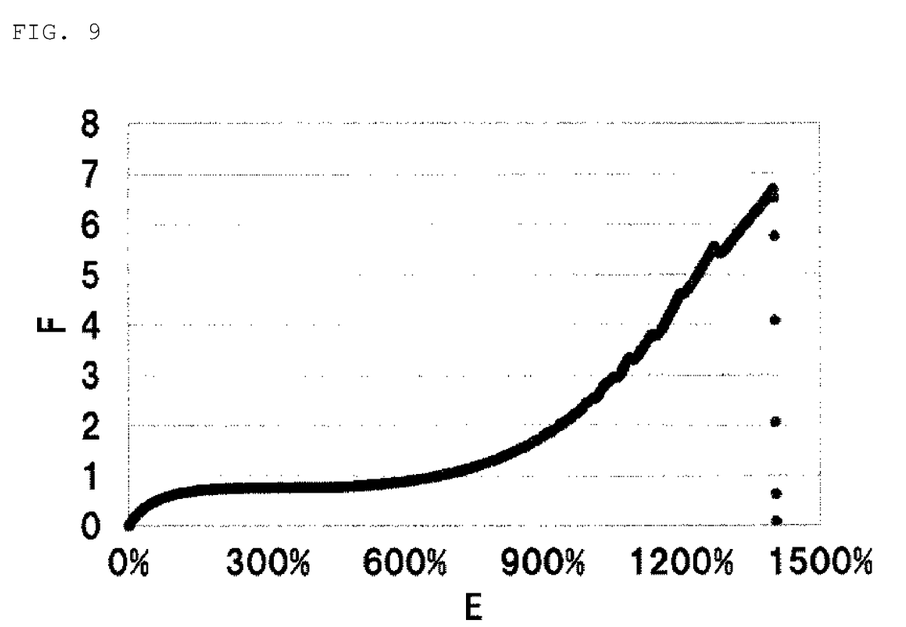
FIG. 9 is a graph of an extension-stress curve of a polymer obtained in Comparative Example 5.

In 30 mL of chloroform, 10 g of the dilactide/ε-caprolactone copolymer obtained in Synthesis Example 2 was dissolved to prepare a polymer solution. The results evaluated by the above-described method are shown in Table 1, and the extension-stress curve is shown in FIG. 9.

TABLE 1

| | Composition | | Evaluation results of film of polymer composition | | |
|---|---|---|---|---|---|
| | Polylactic acid (mass %) | Dilactide/ ε-caprolactone copolymer (mass %) | Young's modulus (MPa) | Maximum point stress (MPa) | Coefficient $r^2$ of determination of flexibility |
| Example 1 | 30 | 70 | 5.4 | 28 | 0.99 |
| Comparative Example 1 | 0 | 100 | 3.9 | 22 | 0.80 |
| Comparative Example 2 | 50 | 50 | 72 | 10 | 0.35 |
| Comparative Example 3 | 70 | 30 | 63 | 11 | 0.72 |
| Comparative Example 4 | 100 | 0 | 53 | 10 | 0.81 |
| Example 2 | 30 | 70 | 0.56 | 17 | 0.99 |
| Example 3 | 40 | 60 | 1.2 | 17 | 0.85 |
| Example 4 | 20 | 80 | 0.53 | 20 | 0.96 |
| Comparative Example 5 | 0 | 100 | 0.76 | 17 | 0.78 |

The invention claimed is:

1. A polymer composition comprising:
polylactic acid; and
a dilactide/ε-caprolactone copolymer,
wherein a content of the polylactic acid relative to a total of 100 mass % of the polylactic acid and the dilactide/ε-caprolactone copolymer is 20 to 40 mass %,
a weight average molecular weight of the polylactic acid is 60,000 or more, and
the dilactide/s-caprolactone copolymer satisfies (1) and (2):
(1) an R value represented by formula (a) is 0.45 or more and 0.99 or less:

$$R = [AB]/(2[A][B]) \times 100 \quad (a)$$

wherein
[A] is a molar fraction (%) of a dilactide residue in the dilactide/ε-caprolactone copolymer,
[B] is a molar fraction (%) of an ε-caprolactone residue in the dilactide/ε-caprolactone copolymer, and
[AB] is a molar fraction (%) of a structure in which a dilactide residue and an ε-caprolactone residue are adjacent to each other (A-B and B-A) in the dilactide/ε-caprolactone copolymer, and
(2) at least one of the dilactide residue and the ε-caprolactone residue has a degree of crystallization of less than 14%.

2. The polymer composition according to claim 1, wherein the dilactide/ε-caprolactone copolymer is composed of two or more macromer units; and wherein the macromer units have a gradient structure in which a dilactide residue and an ε-caprolactone residue form a composition gradient in the skeleton which are linked to each other.

3. The polymer composition according to claim 1, wherein a weight average molecular weight of the dilactide/ε-caprolactone copolymer is 60,000 or more.

4. The polymer composition according to claim 1, wherein a film formed of the dilactide/ε-caprolactone copolymer has a Young's modulus of 6.3 MPa or less and a maximum point stress of 5 MPa or more.

5. The polymer composition according to claim 1, wherein a film formed of the polymer composition has a Young's modulus of 6.3 MPa or less, a maximum point stress of 5 MPa or more, and a coefficient of determination of linear approximation of an extension-stress curve calculated by a tensile test of 0.85 or more.

6. A molded body comprising the polymer composition according to claim 1.

7. A medical instrument comprising the molded body according to claim 6.

8. A nerve regeneration inducing tube at least partially comprising the polymer composition according to claim 1.

9. A polymer composition comprising:
polylactic acid; and
a dilactide/ε-caprolactone copolymer,
wherein a content of the polylactic acid relative to a total of 100 mass % of the polylactic acid and the dilactide/ε-caprolactone copolymer is 20 to 40 mass %,
a film formed of the polymer composition has a Young's modulus of 6.3 MPa or less, a maximum point stress of 5 MPa or more, and a coefficient of determination of linear approximation of an extension-stress curve calculated by a tensile test of 0.85 or more, and
the dilactide/ε-caprolactone copolymer satisfies (1) and (2):

(1) an R value represented by formula (a) is 0.45 or more and 0.99 or less:

$$R = [AB]/(2[A][B]) \times 100 \qquad (a)$$

wherein
- [A] is a molar fraction (%) of a dilactide residue in the dilactide/ε-caprolactone copolymer,
- [B] is a molar fraction (%) of an ε-caprolactone residue in the dilactide/ε-caprolactone copolymer, and
- [AB] is a molar fraction (%) of a structure in which a dilactide residue and an ε-caprolactone residue are adjacent to each other (A-B and B-A) in the dilactide/ε-caprolactone copolymer, and (2) at least one of the dilactide residue and the ε-caprolactone residue has a degree of crystallization of less than 14%.

10. The polymer composition according to claim 9, wherein the dilactide/ε-caprolactone copolymer is composed of two or more macromer units; and wherein the macromer units have a gradient structure in which a dilactide residue and an ε-caprolactone residue form a composition gradient in the skeleton which are linked to each other.

11. The polymer composition according to claim 9, wherein a weight average molecular weight of the dilactide/ε-caprolactone copolymer is 60,000 or more.

12. A molded body comprising the polymer composition according to claim 9.

13. A medical instrument comprising the molded body according to claim 12.

14. A nerve regeneration inducing tube at least partially comprising the polymer composition according to claim 9.

\* \* \* \* \*